(12) United States Patent
Huang

(10) Patent No.: US 9,108,974 B2
(45) Date of Patent: Aug. 18, 2015

(54) PROCESS FOR PREPARING OXYMORPHONE, NALTREXONE, AND BUPRENORPHINE

(75) Inventor: Bao-Shan Huang, Plainsboro, NJ (US)

(73) Assignee: PENICK CORPORATION, Pennsville, NJ (US)

( * ) Notice: Subject to any disclaimer, the term of this patent is extended or adjusted under 35 U.S.C. 154(b) by 1673 days.

(21) Appl. No.: 12/446,172

(22) PCT Filed: Oct. 16, 2007

(86) PCT No.: PCT/US2007/081513
§ 371 (c)(1),
(2), (4) Date: Jul. 12, 2010

(87) PCT Pub. No.: WO2008/048957
PCT Pub. Date: Apr. 24, 2008

(65) Prior Publication Data
US 2010/0274019 A1    Oct. 28, 2010

Related U.S. Application Data

(60) Provisional application No. 60/829,817, filed on Oct. 17, 2006, provisional application No. 61/007,897, filed on Dec. 14, 2006.

(51) Int. Cl.
| C07D 221/28 | (2006.01) |
| C07D 489/08 | (2006.01) |
| A61K 31/44  | (2006.01) |
| C07D 489/02 | (2006.01) |
| C07D 489/04 | (2006.01) |

(52) U.S. Cl.
CPC .............. *C07D 489/08* (2013.01); *A61K 31/44* (2013.01); *C07D 489/02* (2013.01); *C07D 489/04* (2013.01)

(58) Field of Classification Search
CPC .................................................... C07D 221/28
USPC ..................................................... 546/46, 74
See application file for complete search history.

(56) References Cited

U.S. PATENT DOCUMENTS

| 3,332,950 A | 7/1967 | Blumberg et al. |
| 3,433,791 A | 3/1969 | Bentley |
| 3,812,132 A | 5/1974 | Grew et al. |
| 5,071,985 A | 12/1991 | Andre et al. |
| 5,866,164 A | 2/1999 | Kuczynski et al. |
| 5,869,669 A | 2/1999 | Huang et al. |
| 5,922,876 A | 7/1999 | Huang et al. |
| 5,948,788 A | 9/1999 | Huang et al. |
| 5,952,495 A | 9/1999 | Huang et al. |
| 6,008,354 A | 12/1999 | Huang et al. |
| 6,008,355 A | 12/1999 | Huang et al. |
| 6,013,796 A | 1/2000 | Huang et al. |
| 6,067,749 A | 5/2000 | Fist et al. |
| 6,177,567 B1 | 1/2001 | Chiu et al. |
| 6,187,782 B1 | 2/2001 | Nagase et al. |
| 6,262,266 B1 | 7/2001 | Chiu et al. |
| 6,291,675 B1 | 9/2001 | Coop et al. |
| 6,365,742 B1 | 4/2002 | Mudryk et al. |
| 6,376,221 B1 | 4/2002 | Fist et al. |
| 6,395,900 B1 * | 5/2002 | Coop et al. ...................... 546/44 |
| 6,403,798 B2 | 6/2002 | Chiu et al. |
| 6,723,894 B2 | 4/2004 | Fist et al. |
| 6,864,370 B1 | 3/2005 | Lin et al. |
| 6,995,169 B2 | 2/2006 | Chapleo et al. |
| 7,056,527 B2 | 6/2006 | Maruo et al. |
| 7,071,336 B2 | 7/2006 | Francis et al. |
| 7,119,100 B2 | 10/2006 | Zhong et al. |
| 7,129,248 B2 | 10/2006 | Chapman et al. |
| 7,153,966 B2 | 12/2006 | Casner et al. |
| 7,405,301 B2 * | 7/2008 | Scammells et al. ............. 546/44 |
| 7,851,482 B2 | 12/2010 | Dung et al. |
| 8,101,756 B2 | 1/2012 | Eipert et al. |
| 8,134,002 B2 | 3/2012 | Huang |
| 8,217,175 B2 | 7/2012 | Wang et al. |
| 2002/0045755 A1 | 4/2002 | Coop et al. |
| 2006/0009479 A1 | 1/2006 | Bailey et al. |
| 2006/0058333 A1 | 3/2006 | Chapleo et al. |
| 2006/0069113 A1 | 3/2006 | Chapleo et al. |
| 2006/0111383 A1 | 5/2006 | Casner et al. |
| 2006/0173029 A1 | 8/2006 | Chapman et al. |
| 2008/0045716 A1 | 2/2008 | Smith et al. |
| 2008/0125592 A1 | 5/2008 | Huang |
| 2008/0146601 A1 | 6/2008 | Dung et al. |
| 2008/0312441 A1 | 12/2008 | Mannino et al. |
| 2008/0312442 A1 | 12/2008 | Buehler et al. |
| 2009/0270624 A1 | 10/2009 | Weigl et al. |
| 2010/0081814 A1 | 4/2010 | Allen |
| 2010/0081820 A1 | 4/2010 | Jarvi et al. |
| 2010/0087647 A1 | 4/2010 | Allen et al. |
| 2011/0009634 A1 | 1/2011 | Huang |
| 2011/0117172 A1 | 5/2011 | Gopferich |
| 2011/0118466 A1 | 5/2011 | Huang |
| 2011/0269964 A1 | 11/2011 | Bao et al. |
| 2012/0330017 A1 | 12/2012 | Huang |

FOREIGN PATENT DOCUMENTS

| AU | 2007224221 A1 | 9/2007 |
| CA | 1 212 108 | 9/1986 |
| EP | 0359647 | 3/1990 |
| EP | 0 418 591 | 3/1991 |
| EP | 0 915 094 | 5/1999 |

(Continued)

OTHER PUBLICATIONS

Uff et al., "NMR Spectra and Stereochemistry of Some 7-Substituted 6,14-Bridged Thebaine Derivatives" *Magnetic Resonance in Chemistry*, vol. 23, No. 6, pp. 454-459, 1985.

(Continued)

*Primary Examiner* — Yong Chu
*Assistant Examiner* — Sonya Wright
(74) *Attorney, Agent, or Firm* — Greenblum & Bernstein, P.L.C.

(57) ABSTRACT

Methods are provided which include converting oripavine to other opiates, including converting oripavine to naltrexone, buprenorphine, 14-hydroxymorphinone and/or converting 14-hydroxymorphinone to oxymorphone. Purification and salt formation are optionally included.

6 Claims, No Drawings

(56) References Cited

FOREIGN PATENT DOCUMENTS

| EP | 1 439 179 | 7/2004 |
| EP | 2 332 409 | 6/2011 |
| EP | 2 332 410 | 6/2011 |
| EP | 2 073 636 | 9/2012 |
| WO | 82/03768 | 11/1982 |
| WO | 98/02033 | 1/1998 |
| WO | 99/02529 | 1/1999 |
| WO | 01/29048 A2 | 4/2001 |
| WO | 2005/028483 | 3/2005 |
| WO | WO 2005028483 A1 * | 3/2005 |
| WO | 2007/081506 | 7/2007 |
| WO | 2007/103105 A2 | 9/2007 |
| WO | 2010/039216 | 4/2010 |

OTHER PUBLICATIONS

Lansbury et al., "Preparation and Properties of Cyclopropylcarbinyllithium" *J. Am. Chem. Soc.*, vol. 86, pp. 2247-2251, 1964.

Strategic Applications of Named Reactions in Organic Synthesis, Background and Detailed Mechanisms, by Laszlo Kurti and Barbar Czako, Elsevier Academic Press, copyright 2005, Finkelstein Reaction, pp. 170-171.

San Filippo et al., "Free-Radical Participation in the Reactions of Selected Metalate Anions with Alkyl Halides" *J. Am. Chem. Soc.*, vol. 100, pp. 4834-4842, 1978.

Michiels, L. *Chemisches Zentralblatt*, vol. 82, No. 1, pp. 66-67, 1911.

U.S. Appl. No. 13/407,271 to Huang, filed Feb. 28, 2012.

U.S. Appl. No. 13/407,298 to Huang, filed Feb. 28, 2012.

U.S. Appl. No. 12/446,171 which is the National Stage of PCT/US07/68009 to Bao-Shan Huang, filed May 2, 2007 and entitled "Process for Preparing Oxymorphone."

U.S. Appl. No. 11/873,093, filed Oct. 16, 2007 and entitled "Process for Preparing Oxymorphone, Naltrexone, and Buprenorphine."

Extended European Search Report issued with respect to European App. No. 10166419.1, dated Apr. 27, 2011.

Extended European Search Report issued with respect to European App. No. 10166417.5, dated Apr. 21, 2011.

Marton et al., "Herstellung von 6,14-Ethenomorphinan-Derivaten" *Liebigs Ann. Chem.*, pp. 915-919, 1993.

Klein et al., "Electrophilic α-Methylene-γ-lactone and Isothiocyanate Opioid Ligands Related to Etorphine" *J. Med. Chem.*, vol. 33, pp. 2286-2296, 1990.

Schwartz et al., "Efficient Synthesis of 14-Hydroxymorphinans from Codeine" *J. Med. Chem.*, vol. 24, No. 12, pp. 1525-1528, 1981.

Krassnig et al., "Optimization of the Synthesis of Oxycodone and 5-Methyloxycodone", *Archiv der Pharmazie*, vol. 329, No. 6, p. 325-326 (1996).

Freund et al., "Uber die Umwandlung von Thebain in Oxycodeinon and dessen Derivate", *Journal fur Praktische Chemie*, vol. 94, p. 135-178 (1916).

Seki, Isao, "Studies on the Morphine Alkaloids and Its Related Compounds. XVII. One-Step Preparations of Enol Ether and Pyrrolidinyl Dienamine of Normorphinone Derivatives", *Chemical & Pharamceutical Bulletin*, vol. 18, No. 4, p. 671-676 (1970).

Hauser et al., "14-Hydroxycodeinone. An Improved Synthesis", *Journal of Medicinal Chemistry*, vol. 17, No. 10, p. 1117 (1974).

Iijima et al., "213. The Oxidation of Thebaine with m-Chloroperbenzoic Acid. Studies in the (+)-Morphinan Series. III", *Helvetica Chimica Acta*, vol. 60, p. 2135-2137 (1977).

Australian Examination Report dated Aug. 22, 2011 for patent family member Australian Patent Application No. 2007311152.

Australian Examination Report dated Aug. 22, 2011 for patent family member Australian Patent Application No. 2007313103.

European Office Action issued in connection with European Application EP 07 84 0163.5, dated Dec. 21, 2009.

Andre et al., "O-Demethylation of Opioid Derivatives with Methane Sulfonic Acid / Methionine: Application to the Synthesis of Naloxone and Analogues" *Synthetic Communications*, vol. 22, No. 16, pp. 2313-2327, 1992.

Hosztafi, "Reactions of Azodicarboxylic Esters with Amines" *Scientia Pharmaceutica*, vol. 55, pp. 61-75, 1987.

Marton et al., "Herstellung von 6,14-Ethenomorphinan-Derivaten" *Monatshefte für Chemie*, vol. 125, pp. 1229-1239, 1994.

Coop et al., "L-Selectride as a General Reagent for the O-Demethylation and N-Decarbomethoxylation of Opium Alkaloids and Derivates" *Journal of Organic Chemistry* vol. 63, No. 13, pp. 4392-4396 (1998).

Weiss, U., "Derivatives of Morphine. II Demethylation of 14-hydroxycodeinone, 14-Hydroxymorphinone and 8,14-Dihydroxydihydromorphinone" *Journal of Organic Chemistry* No. 22, pp. 1505-1508 (1957).

Supplementary European Search Report issued in connection with European Application EP 07 85 4091, dated Oct. 20, 2009.

Supplementary European Search Report issued in connection with European Application EP 07 84 0163, dated Oct. 16, 2009.

U.S. Appl. No. 13/013,569 to Huang, filed Jan. 25, 2011.

European Office Action that issued with respect to patent family member European Patent Application No. 07840163.5 on Mar. 18, 2011.

Michiels, L. *Chemisches Zentralblatt*, vol. 82, No. 1, p. 66-67, 1911, along with an English language translation thereof.

Freund et al., "Über die Umwandlung von Thebain in Oxycodeinon and dessen Derivate" *Journal für Praktische Chemie*, vol. 94, p. 135-178, 1916.

Grant & Hackh's Chemical Dictionary (5th Ed., 1987) at pp. 23 and 148.

European Office Action issued with respect to patent family member European Patent App. No. 10166419.1, dated May 8, 2013.

Canadian Office Action issued with respect to patent family member Canadian Patent App. No. 2,674,915, dated Mar. 27, 2013.

Laduron et al., "Efficient and Scalable Method for the Selective Alkylation and Acylation of Secondary Amines in the Presence of Primary Amines" *Organic Process & Development* 9:102-104, 2005.

Calgary. URL: http://www.chem.ucalgary.ea/courses/351/Carey5th/Ch08/ch8-7html, (updated Jan. 29, 2003). Accessed online Jan. 28, 2013.

Smith, M.B. And March., J. John Wiley & Sons, Inc, "March's Advanced Organic Chemistry—Reactions, Mechanisms, and Structure" Sixth Edition, 2007, p. 574-575.

Caron, S., John Wiley & Sons, Inc, "Practical Synthetic Organic Chemistry—Reactions, Principles, and Techniques" 2011, 30 (Chapter 1.4.1.1).

U.S. Appl. No. 14/060,759 to Huang, filed Oct. 23, 2013.

Examination Report issued with respect to patent family member AU App. No. 2012216358, mailed Oct. 29, 2013.

Coop et al., "Direct and Simple O-Demethylation of Thebaine to Oripavine," *J. Org. Chem.* 61:6774, 1996.

Comprehensive Organic Synthesis, B. Trost and I. Fleming (Editors), vol. 7, p. 372, Pergamon Press (now Elsevier), 1991.

Ullmann's Encyclopedia of Industrial Chemistry, 5$^{th}$ Edition, vol. A19, pp. 206-210, 1991.

Organic Peroxides, Daniel Swern (Editor), vol. I, pp. 337-338, Wiley, 1970.

Vogel's Textbook of Practical Organic Chemistry, 5$^{th}$ Edition, pp. 455-457, 1989.

Printouts from Wikipedia: meta-chloroperoxybenzoic acid, performic acid, May 23, 2013 (5 pages).

Printout from Sigma-Aldrich online catalogue: peracetic acid solution, May 22, 2013 (1 page).

Printouts from Sigma-Aldrich online catalogue: 3-chloroperbenzoic acid and performic acid, May 23, 2013 (3 pages).

Communication of a Notice of Opposition with respect to EP Patent No. 2073636, dated Jun. 19, 2013.

* cited by examiner

PROCESS FOR PREPARING OXYMORPHONE, NALTREXONE, AND BUPRENORPHINE

CROSS-REFERENCE TO RELATED APPLICATIONS

This application claims priority to U.S. Provisional Application No. 60/829,817, filed Oct. 17, 2006, and to U.S. Provisional Application No. 61/007,897, filed Dec. 14, 2006, for which a Request to Convert Non-Provisional Application to Provisional Application Under 37 C.F.R. §1.53(c)(2) was filed Oct. 11, 2007, from U.S. application Ser. No. 11/611,049, filed Dec. 14, 2006, the disclosures of each of which is incorporated herein by reference in its entirety.

BACKGROUND OF THE INVENTION

1. Field of the Invention

This invention relates to preparation of opiates such as 14-hydroxymorphinone, oxymorphone, naltrexone, methylnaltrexone, buprenorphine, nalmefene, nalorphine, and naloxone from oripavine.

2. Background of the Invention and Related Art

Oxymorphone, a potent opiate analgesic, is a semi-synthetic substitute for morphine. It is about ten times as potent as morphine. In the United States, FDA has approved oxymorphone hydrochloride in oral, parenteral and suppository forms. Naltrexone, methylnaltrexone, buprenorphine, nalmefene, nalorphine, and naloxone are other useful opiates.

Oxymorphone can also be converted to these and other useful compounds, such as nal-compounds, including naloxone.

Oxymorphone is typically synthesized using thebaine, morphine or another compound as a starting material. Thebaine, when used, is generally obtained from the concentrated poppy straw (CSP-T), a poppy extract relatively rich in thebaine. Reaction schemes for producing oxymorphone from thebaine take several steps, to intermediates such as oxycodone, then conversion of the 3-methoxy group of oxycodone to the 3-hydroxy group of oxymorphone. U.S. Pat. No. 6,291,675, for example, discloses a method for O-demethylation of the 3-methoxy group of opiates by use of a lithium hydride compound, providing a yield of O-demethylated opioid of at least 23%. U.S. Pat. No. 5,922,876 discloses preparation of oxymorphone from morphine. The process includes protection of the 3-hydroxy group of morphine with an aceto or benzyl group.

Naltrexone is a narcotic antagonist; it also has been used to treat opioid abuse and alcoholic abuse. It can be prepared from thebaine (U.S. Pat. No. 3,332,950) or morphine (U.S. Pat. No. 6,013,796). Buprenorphine is a narcotic agonist/antagonist; it has been used for the treatment of opioid abuse. It can be prepared from thebaine (U.S. Pat. No. 3,433,791).

Features and advantages of the present invention will be set forth in the description of invention that follows, and will be apparent, in part, from the description or may be learned by practice of the invention. The invention will be realized and attained by the compositions, products, and methods particularly pointed out in the written description and claims hereof.

DETAILED DESCRIPTION OF THE PREFERRED EMBODIMENTS

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

Unless otherwise noted, all reactions are run under inert conditions, such as under nitrogen or argon for safety and/or to avoid the formation of N-oxide by-products.

The present inventor has discovered that oripavine can be economically converted to other opiates, such as oxymorphone, naltrexone, and buprenorphine and derivatives thereof. Any starting material comprising oripavine may be used. The starting material preferably comprises greater than about 50% by weight oripavine, preferably greater than about 70%, more preferably greater than about 95%. The starting material is preferably purified oripavine, or a concentrate of poppy straw comprising oripavine as the main alkaloid (hereinafter, "CPS-O").

Preferably, the oripavine comprises "natural oripavine," but can comprise oripavine from any source. By "natural oripavine" is meant oripavine obtained from a natural source (e.g., botanical, bioengineered bacterial, etc.), and is meant to distinguish from oripavine obtained in a laboratory or factory setting by partial or total chemical synthesis, e.g., synthetic or semi-synthetic oripavine. Natural oripavine includes, without limitation, CPS-O, and purified oripavine obtained from CPS-O or other poppy straw.

Preparation of Oxymorphone

Preferably, oripavine is oxidized with an oxidizing agent to obtain 14-hydroxymorphinone. The 14-hydroxymorphinone is then preferably reduced with a reducing agent to obtain oxymorphone. The 14-hydroxymorphinone can also be used in other ways, preferably to prepare other products.

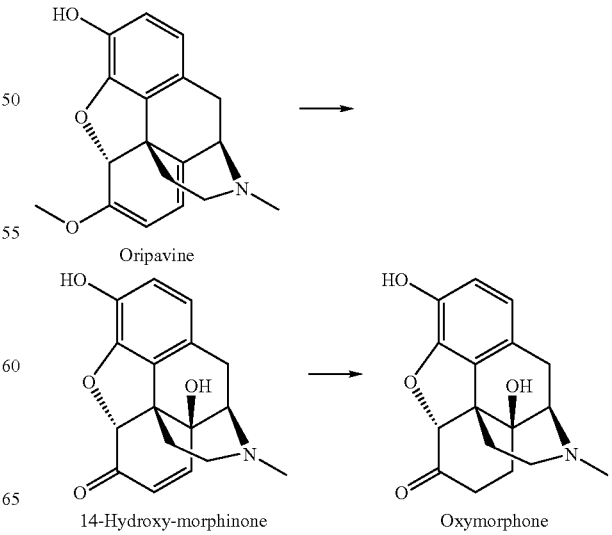

The oxidizing agent can comprise any oxidizing agent that permits the conversion of oripavine to 14-hydroxymorphinone, including, but not limited to, peroxy acids, such as performic acid, peracetic acid, and m-chloroperoxybenzoic acid (MCPBA). Mixtures of oxidizing agents may be used. When a peroxy acid is used, it may be added, or prepared in situ.

When the oxidizing agent comprises a peroxy acid prepared in situ, it may be prepared in any manner, preferably by combining a peroxide and an acid. Any peroxide or combination of, peroxides that can provide a peroxy acid can be used, preferably hydrogen peroxide, for example, aqueous hydrogen peroxide. Any acid or combination of acids that can provide a peroxy acid can be used, preferably formic acid, or acetic acid, for example, aqueous solutions of formic and/or acetic acid. Performic acid may be obtained, for example, by combining hydrogen peroxide and formic acid, and peracetic acid may be obtained by combining hydrogen peroxide with acetic acid.

The reaction may be carried out in any appropriate solvent, preferably an aqueous solvent. When the oxidizing agent includes a peroxy acid, it is preferred to use a solvent comprising the corresponding acid. For example, when the oxidizing agent comprises performic acid, it is preferred to use a solvent comprising formic acid, and when the oxidizing agent comprises peracetic acid, it is preferred to use a solvent comprising acetic acid. When MCPBA is used, it is preferred to use a solvent comprising acetic acid.

An exemplary process using performic acid as oxidizing agent is:

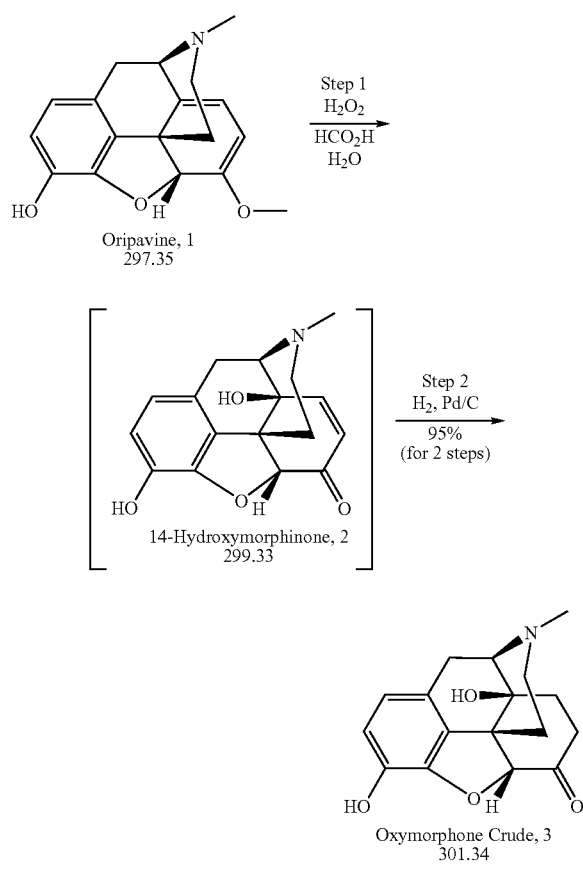

An exemplary process using MCPBA as oxidizing agent is:

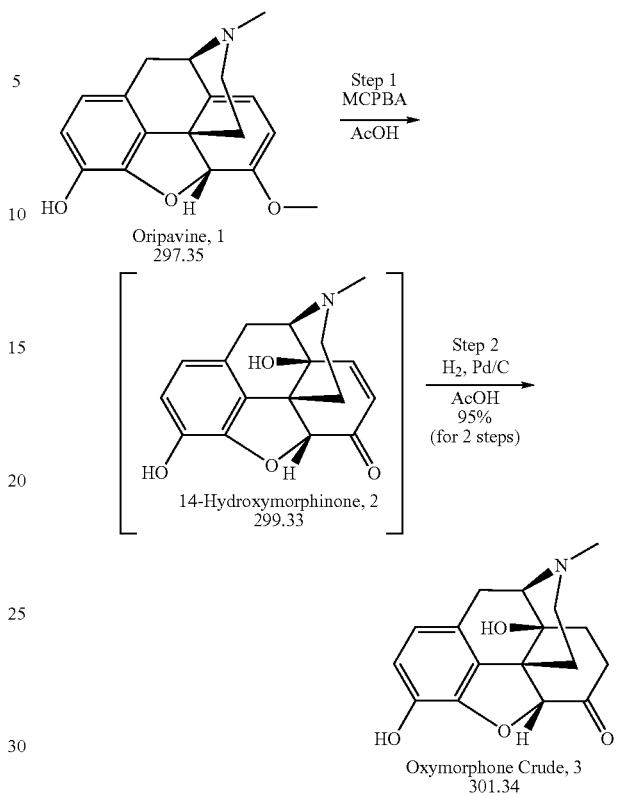

Any temperature that permits the reaction to proceed may be used. The temperature need not remain constant, and may vary during the reaction. Higher reaction temperatures speed up the reaction, but may increase formation of by-products. Different oxidation agents may run optimally at different temperatures. Reactions employing performic acid, for example are preferably run in the range of about 20 to 60° C., more preferably about 40-50° C., even more preferably at about 50° C. Reactions employing MCPBA are preferably run in the range of about 0 to 40° C., more preferably about 10-30° C., even more preferably at about ambient temperature, e.g., about 25° C.

The reaction is run under conditions to convert oripavine to 14-hydroxymorphinone. Preferably, at least about 90% of the oripavine is converted to 14-hydroxymorphinone, more preferably, about 95%, even more preferably about 98% or 99%. Preferably, the conversion of oripavine to 14-hydroxymorphinone will be about 100%.

The remaining amount of oripavine in the reaction mixture, as well as the amount of 14-hydroxymorphinone produced, can be determined by any method, such as by TLC or HPLC.

Any reducing agent may be used to convert 14-hydroxymorphinone to oxymorphone. Catalytic hydrogenation is a preferred method, e.g., with a palladium catalyst, preferably palladium, or palladium hydroxide, on activated carbon (e.g., Pd/C).

Catalytic hydrogenation may be performed at any suitable pressure, and is preferably done completely, or in part, in a low pressure environment. Catalytic hydrogenation preferably includes hydrogenation at or greater than, about 1 atmosphere pressure. By "low pressure" is preferably meant less than about 10 atm, or less than about 4 atm, Catalytic hydrogenation reactions, therefore, include hydrogenation at, e.g., at about 1-10 or about 1-4 atm. Low pressure hydrogenation generally requires less expensive processing and/or lower equipment costs than hydrogenation at higher pressures.

The oxidizing and reduction may be performed as a "one pot" process, or may be done in separate vessels. The 14-hydroxymorphinone may be isolated, but need not be isolated, prior to reduction. In a preferred embodiment, the 14-hydroxymorphinone is not isolated in solid form prior to reduction.

Preferably, the opiate, e.g., oxymorphone, or a salt thereof, is purified. Preferably, crude oxymorphone is isolated, purified, and converted to a salt, preferably the hydrochloride salt. An exemplary process for purifying crude oripavine base is:

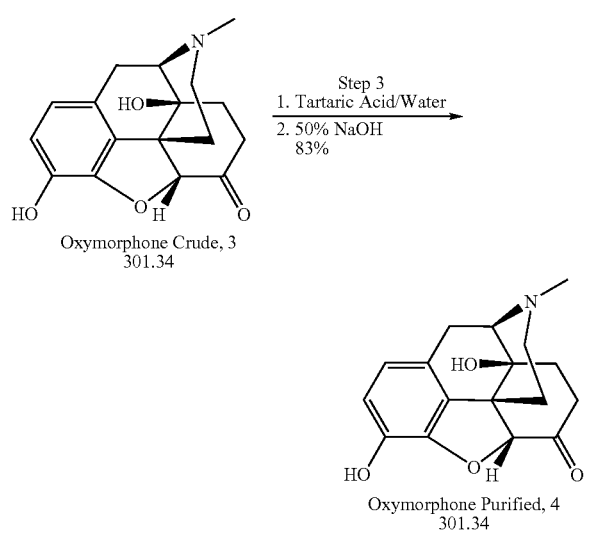

Purification aids may be used in the purification process. Preferred purification aids include adsorbents. Some preferred purification aids include activated carbon (commercially available as, e.g., DARCO), and/or powdered cellulose (commercially available as, e.g., SOLKA-FLOC). The reducing agent sodium bisulfite may be used, e.g., when performing the reaction in the presence of oxidants, e.g., under an oxidizing atmosphere. When the reaction is run under a non-oxidizing atmosphere, e.g., nitrogen gas, it may be possible to omit sodium bisulfite. Other purification aids, including purification aids known in the art, may be selected and used by a person of ordinary skill in the art. Purified oxymorphone, containing very little 14-hydroxymorphinone, is especially desirable because the impurity (14-hydroxymorphinone) is an alpha-beta-unsaturated ketone, which may be a carcinogen.

Opiate salts, e.g. of oxymorphone, may also be prepared. Any salt, preferably a therapeutically acceptable salt, may be included in the present invention. The hydrochloride is a preferred salt. Methods for preparing salts of compounds are known in the art. An exemplary process for preparing the hydrochloride salt of purified oxymorphone is:

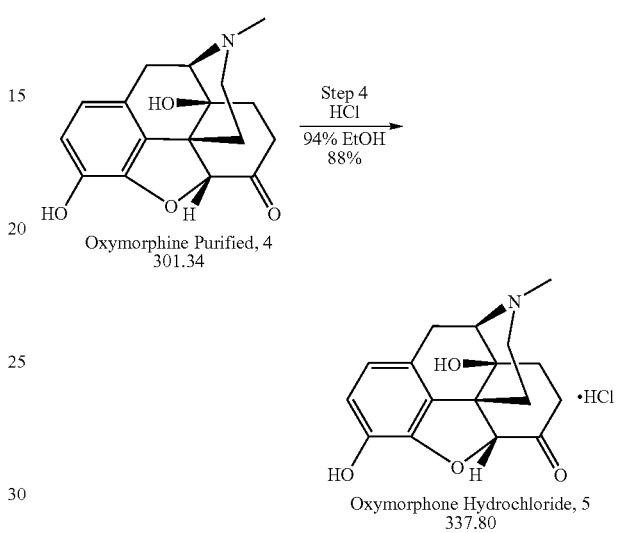

Generally, oxymorphone, preferably purified oxymorphone, is suspended or dissolved in a liquid, preferably an alcohol and/or water; and more preferably ethanol, 2-propanol, combinations thereof, and combinations with water. Then, an acid, such as hydrochloric acid (preferably concentrated or gaseous HCl), is added to the mixture at a higher temperature. After cooling for a period of time, preferably once the reaction is complete or substantially complete, the oxymorphone salt is separated from the mixture, washed, and dried.

Oxymorphone can also be converted to other compounds, such as naloxone. Methods for effecting this conversion are known in the art.

Preparation of Naltrexone

Oripavine can also be converted to naltrexone. One scheme for performing this conversion is shown in Scheme 1, below:

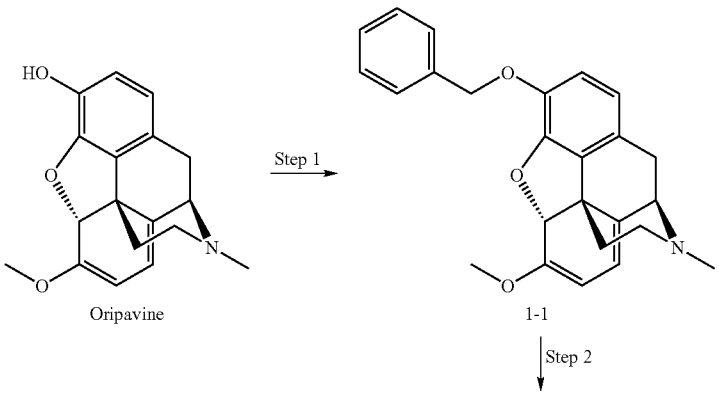

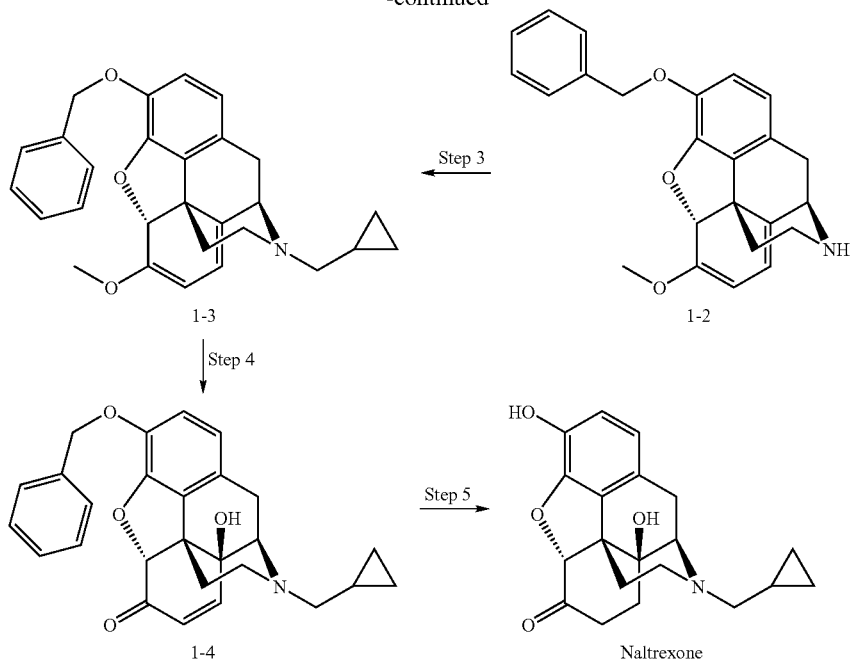

Generally, the phenolic hydroxyl group in the 3-position of oripavine can be protected, for example by a benzyl group (or a substituted benzyl group, etc.) to 3-benzyloripavine, (1-1), followed by N-demethylation with a demethylation agent such as 1-chloroethyl chloroformate (ACE-Cl), and then reacting with methanol to obtain 3-benzyl-nororipavine, (1-2). The nor-product is alkylated with (chloromethyl)cyclopropane (or other halomethylcyclopropane, or tosylmethylcyclopropane, for example) to give 3-benzyl-17-cyclopropylmethylnororipavine, (1-3). This is oxidized to 3-benzyl-17-cyclopropylmethyl-14-hydroxynororipavine, (1-4), by reacting with an oxidation agent such as a peroxy acid like peroxyformic acid, peroxyacetic acid, or MCPBA. The product, which may or may not be isolated, can be hydrogenated to reduce the 7,8-double bond and to de-benzylate at the same time to give naltrexone, which can be converted to a salt.

Preparation of Buprenorphine

Oripavine can also be converted to buprenorphine. One scheme for performing this conversion is shown in Scheme 2, below:

Scheme 2. Synthesis of Buprenorphine from Oripavine (such as obtained from CPS-O)

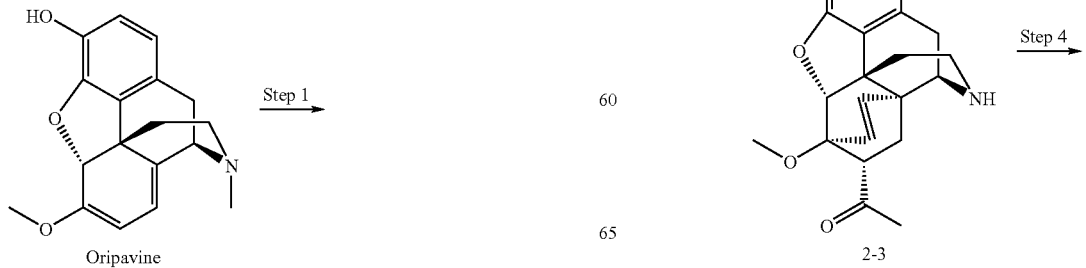

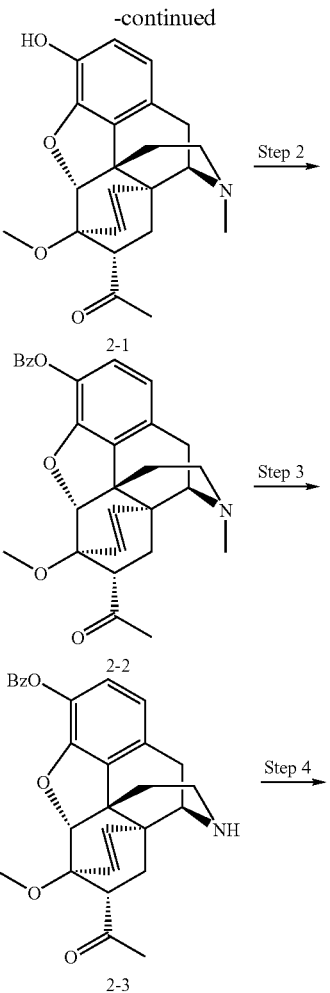

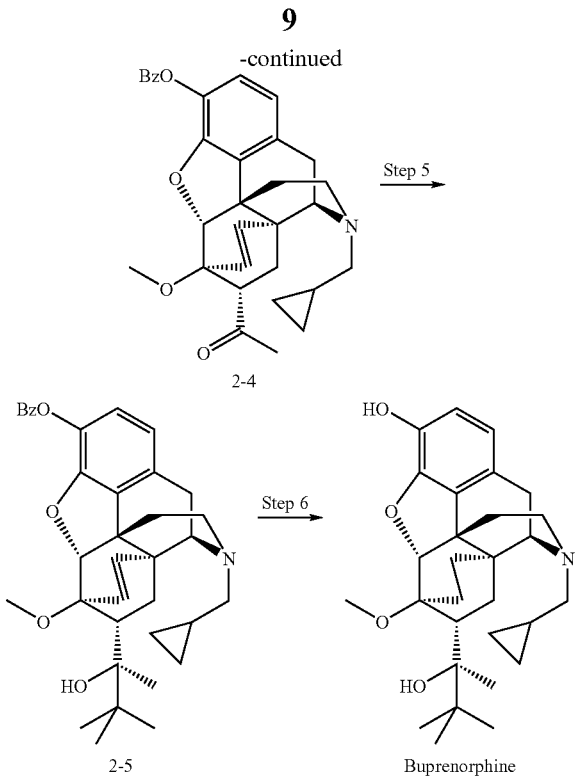

Generally, oripavine can be reacted with methyl vinyl ketone under Diels Alder conditions to give 7α-acetyl-6,7,8,14-tetrahydro-6,14-endoethenooripavine, (2-1), which can be protected for the 3-phenolic hydroxyl group by, for example, a benzyl group (or a substituted benzyl group, etc.) to 7α-acetyl-3-benzyl-6,7,8,14-tetrahydro-6,14-endoethenooripavine, (2-2). This is de-methylated by reacting with a demethylating agent, such as ACE-Cl, and then refluxing in methanol to the nor product 7α-acetyl-3-benzyl-6,7,8,14-tetrahydro-6,14-endoethenonororipavine, (2-3), which is alkylated with (chloromethyl)-cyclopropane (or other halomethylcyclopropane, or tosylmethylcyclopropane, for example) to 7α-acetyl-3-benzyl-17-cyclopropylmethyl-6,7,8,14-tetrahydro-6,14-endoethenonororipavine, (2-4). This is reacted with a Grignard reagent, tert-butyl magnesium chloride (or tert-butyl lithium), in THF to 3-benzyl-17-cyclopropylmethyl-6,14-endo-etheno-7α-(2-hydroxy-3,3-dimethyl-2-butyl)-6,7,8,14-tetrahydronororipavine, (2-5), which is reduced and de-benzylated at the same time by hydrogenation with Pd/C or Pd(OH)$_2$ in hydrogen to buprenorphine, which can be converted to a salt.

Alternatively, the hydroxyl group of oripavine is protected with a benzyl group first and then reacted with methyl vinyl ketone under Diels Alder conditions.

Oxymorphone, naltrexone, or buprenorphine, or salts thereof, preferably HCl salts, may be prepared into pharmaceutical dosage forms. Pharmaceutical dosage forms include, but are not limited to, tablets, pills, capsules (including hard or soft gelatin capsules), parenteral formulations, suppositories, patches, and powders. Generally, a salt, e.g., the hydrochloride, is preferred. Oxymorphone base may be used, e.g., for transdermal patches. Preferred dosage forms include parenteral formulations and suppositories.

Pharmaceutical dosage forms comprising, e.g., oxymorphone, naltrexone, or buprenorphine, may include one or more pharmaceutically acceptable excipients, and can be selected by those of ordinary skill in the art. Pharmaceutically acceptable excipients include, but are not limited to, carrier vehicles, stabilizing agents, solubilizing agents, lubricating agents, flow agents, bulking agents, control release agents, disintegrating agents, binding agents, pigments, flavoring agents, and coating agents.

EXAMPLES

Synthesis of Oxymorphone

Example 1

Crude Oxymorphone from Oripavine

To a stirred oripavine (166.7 mg; 0.561 mmol) solution in 0.5 mL 30% formic acid (4.185 mmol) was added 0.1 ml 30% hydrogen peroxide (0.979 mmol), and the resulting mixture was stirred at 50° C. After complete transformation as indicated by TLC, the reaction mixture was transferred to a Parr Shaker, and 5% Pd/C (51.9 mg) was added. The mixture was hydrogenated at room temperature under 28 inch-Hg overnight, filtered, basified with NH$_4$OH, and extracted with methylene chloride (5×15 ml). The extract was evaporated under reduced pressure to give 113.4 mg of a pale yellow solid, yield 67.1%. The product has an identical retention time in HPLC and same R$_f$ value in TLC to an oxymorphone standard.

Example 2

Crude Oxymorphone from Oripavine

Oripavine (50.0 g, 168 mmol), de-ionized water (70 ml), and 90% formic acid (42.0 g, 0.821 mol) were charged into a 500 ml 3-necked round bottom flask. The solution was stirred at 30-40° C. and to the composition was added 35% hydrogen peroxide, drop-wise (19.7 g, 0.203 mol), while keeping the temperature below 40° C. Upon completion of the addition, the mixture was stirred at 40-50° C. for 4 hours. The reaction mixture was transferred to a 1-L hydrogenation vessel and 5% Pd/C (3.2 g) and 2-propanol (160 ml) were added. Hydrogenation proceeded at 46-52 psig at room temperature overnight (about 18 h). The catalyst in the mixture was filtered off. The filtrate and washings are combined and basified with 50% NaOH (59.6 g) to pH 9.16. The temperature was kept at below 30° C. during the basification. The slurry was stirred at room temperature for 1 hour, and filtered to give a brown solid, which was then dried at 90° C. and 25" Hg vacuum overnight to provide the crude oxymorphone as light brown solids (48.2 g, 160 mmol, 95.2% yield).

Example 2b

Crude Oxymorphone from Oripavine

Oripavine (50.0 g, 168 mmol), was converted to 14-hydroxymorphinone as in Example 2 through and including addition of hydrogen peroxide. Upon completion of the addition, the mixture was stirred at 40-50° C. By HPLC, it was determined that the area ratio of 14-hydroxymorphinone:oripavine is 27.2:72.8 after 1 hour, and 99.3:0.7 after 4 hours. After 4 hours 40 minutes, the reaction mixture was transferred to a 1-L hydrogenation vessel and 5% Pd/C (3.2 g) (Degussa E101 o/w, H$_2$O 56.2%) was added. Hydrogenation proceeds at 46-52 psig at room temperature overnight (about 18 h). The mixture was filtered, and rinsed with about 50 ml water. 250 ml of filtrate was obtained, to which was added 25 ml butanol, yielding a mixture having pH of 2.86. While kept at less than 30° C., or at about 19.6° C., the filtrate was basified with 57.5 g of 50% NaOH, resulting in a pH of 9.05. The mixture was stirred for about one hour at room temperature, filtered, washed with water (4×50 ml), yielding a brown solid. The wet cake was dried at 93° C. at 25" Hg overnight, yielding 44.2 g, 87.2% yield, of oxymorphone as a light brown solid.

Example 3

Crude Oxymorphone from CPS-O

A mixture of CPS-O (6.92 g contains 76% (5.26 g, 17.7 mmol) of oripavine), meta-chloroperoxybenzoic acid (MCPBA, 4.30 g) and glacial acetic acid (52 ml) is stirred at room temperature for 5 hours. The amount of oripavine is then expected to be not more than 1% by HPLC analysis. To the resulting 14-hydroxymorphinone mixture is added 5% Pd/C (0.55 g) and hydrogenation proceeds at room temperature at 48 psig of hydrogen for about 18 hours. The amount of unreacted 14-hydroxymorphinone is expected to be not more than 0.5% by HPLC analysis. The mixture is filtered to remove the catalyst and the filtrate is evaporated to almost dryness. The residue is dissolved in water and basified to pH 9 by ammonium hydroxide. The solids are collected by filtration and dried at 90° C. and under 25-inch Hg of vacuum for 3 hours to give crude oxymorphone (approximately 95% yield expected).

Example 4

Purified Oxymorphone

A suspension of the crude oxymorphone (20.0 g, 66 mmol) and water (120 ml) was stirred at 45-55° C. Tartaric acid (5.5 g) was added to adjust the pH to 4.35 to complete dissolution. DARCO (1.0 g) and SOLKA-FLOC (1.0 g) were added and stirred at 45-55° C. for 1 hour. The mixture was filtered and rinsed with water (10 ml). The filtrate and washings were combined and to this were added DARCO (1.0 g), SOLKA-FLOC (1.0 g) and sodium bisulfite (0.4 g). The mixture was stirred for 1 hour at 45-55° C., filtered and rinsed with water (10 ml). 1-BuOH (12 ml) was added to the filtrate and stirred at 45-55° C. 50% NaOH (6.1 g) was added to adjust the pH to 8.56 at 45-55° C., in particular, 50.5° C. The slurry was cooled to room temperature and filtered. Light brown solids were collected and dried at 65° C. and 25" Hg vacuum overnight to give purified oxymorphone (18.2 g, 60 m mol, 91.0% yield).

Example 5

Oxymorphone HCl from Purified Oxymorphone

Purified oxymorphone (17.8 g, 59 mmol) was suspended in 94% aq. ethanol (107 ml) and stirred at 50-60° C. Concentrated hydrochloric acid (32%) was added slowly to adjust the pH to 2.58. The mixture was allowed to cool to room temperature, and then cooled further to 0-10° C., stirred for 2 hours and filtered then washed with ethanol (3×20 ml). The isolated solids were dried at 75° C. under 25 inches-Hg overnight to give oxymorphone HCl as white solids (17.3 g, 51 mmol, 86.7% yield).

This Oxymorphone HCl meets the specifications in the USP 2006 monograph for Oxymorphone Hydrochloride.

Synthesis of Naltrexone

Example 6

Preparation of 3-Benzyloripavine (1-1) from CPS-O

A mixture of CPS-O (76% Oripavine, 13.16 g, 44 m mol), benzyl bromide (9.2 g) and potassium bicarbonate (17.6 g) in toluene (200 ml) is heated to reflux for 4 hours, then cooled and filtered. The filtrate is extracted with dilute acetic acid. Immediately, the extract is basified with ammonium hydroxide to collect 3-benzyloripavine (expected yield: 16.19 g; 95% yield).

Example 7

Preparation of 3-Benzyl-17-cyclopropylmethylnororipavine (1-3) through 3-Benzylnororipavine (1-2) from 3-Benzyloripavine (1-1)

A solution of 3-benzyloripavine (11.62 g, 30 mmol), 1-chloroethyl chloroformate (5.52 g, 37.8 mmol) and proton sponge (1.1 g) in methylene chloride (80 ml) is heated at reflux for 2 hours. The reaction mixture is evaporated in vacuo to dryness. The residue is dissolved in methanol (50 ml), heated to reflux for 30 minutes, basified with ammonium hydroxide, and then evaporated to dryness. To the residue is added (chloromethyl)-cyclopropane (5.14 g, 55.6 m mol), sodium carbonate (14.7 g, 139 mmol), and potassium iodide (4.6 g, 28 mmol) in ethanol (250 ml) and heating proceeds at reflux for 20 hours. The mixture is cooled and evaporated in vacuo to dryness. The residue is basified with ammonium hydroxide and extracted with methylene chloride. The extract is washed with water, dried with anhydrous sodium sulfate, and evaporated in vacuo to dryness. The residue is chromatographed on silica gel with a eluting solvent system of methanol/ethyl acetate (10/90 v/v) to give 3-benzyl-17-cyclopropylmethylnororipavine (expected yield: 10.93 g; 85% yield).

Example 8

Preparation of naltrexone through 3-benzyl-17-cyclopropylmethyl-14-hydroxynormorphinone (1-4) from 3-benzyl-17-cyclopropylmethylnororipavine (1-3)

A mixture of 3-benzyl-17-cyclopropylmethylnororipavine (10 g, 23 mmol), formic acid (90%, 60 ml), D.I. water (3 ml), methanol (10 ml) and hydrogen peroxide (31%, 3.3 ml) is stirred and heated at 40-50° C. for 5 hours. The mixture is allowed to cool, then 5% Pd/C (0.5 g) is added, and the mixture is hydrogenated under 25-inch-Hg for 8 hours. The catalyst is filtered off. The residue is evaporated in vacuo to dryness to give a crude product, which is re-crystallized from acetone/water to give a white crystalline solid. It is dried at 90° C. under 25 inch-Hg of vacuum for 4 hours to give naltrexone (expected yield: 6.8 g; 86% yield). This product is identical to a USP standard of Naltrexone.

Synthesis of Buprenorphine from CPS-O or Oripavine

Example 9

Preparation of 7α-Acetyl-6,7,8,14-tetrahydro-6,14-endo-ethenooripavine (2-1) from Oripavine A mixture of oripavine (28.7 g, 96.5 mmol) and methyl vinyl ketone (18 ml) in 2-propanol (90 ml) is stirred and heated at reflux for 6 hours. The mixture is cooled to 10° C. and the solids filtered off, washed with cold 2-propanol and dried at 50° C. to produce an anticipated yield of 32.9 g (93% yield) of 7α-acetyl-6,7,8,14-tetrahydro-6,14-endo-ethenooripavine.

Example 10

Preparation of 7α-acetyl-3-benzyl-6,7,8,14-tetrahydro-6,14-endo-ethenooripavine (2-2) from 7α-acetyl-6,7,8,14-tetrahydro-6,14-endo-ethenooripavine (2-1)

A mixture of 7α-acetyl-6,7,8,14-tetrahydro-6,14-endo-ethenooripavine (20.5 g, 55.8 m mol), benzyl bromide (11.5 g), and sodium carbonate (23.6 g) in toluene (350 ml) is heated at reflux for 4 hours. The reaction mixture is cooled and washed with water. The organic layer is evaporated in vacuo to dryness to give 7α-acetyl-3-benzyl-6,7,8,14-tetrahydro-6,14-endo-ethenooripavine (24.5 g, 96% yield).

Example 11

Preparation of 7α-acetyl-3-benzyl-17-cyclopropylmethyl-6,7,8,14-tetrahydro-6,14-endo-ethenonororipavine (2-4) through 7α-acetyl-3-benzyl-6,7,8,14-tetrahydro-6,14-endo-ethenonororipavine (2-3) from 7α-acetyl-3-benzyl-6,7,8,14-tetrahydro-6,14-endo-ethenooripavine (2-2)

A solution of 7α-acetyl-3-benzyl-6,7,8,14-tetrahydro-6,14-endo-ethenooripavine (6.9 g, 15 m mol), 1-chloroethyl chloroformate (2.76 g, 19 m mol) and proton sponge (0.5 g) in methylene chloride (50 ml) is heated at reflux for 2 hours. The reaction mixture is evaporated in vacuo to dryness. The residue is dissolved in methanol (30 ml). To this is added a few drops of concentrated hydrochloric acid and heated to reflux for 30 minutes and basified with ammonium hydroxide. This is evaporated to dryness. To the residue is added (chloromethyl)-cyclopropane (2.07 g, 28 mmol), sodium carbonate (7.4 g, 64 mmol), and potassium iodide (2.3 g, 14 mmol) in ethanol (150 ml) and heated at reflux for 20 hours, The resulting mixture is cooled and evaporated in vacuo to dryness. The residue is basified with ammonium hydroxide and extracted with methylene chloride. The extract is washed with water, dried with anhydrous sodium sulfate and evaporated in vacuo to dryness. The residue is chromatographed on silica gel with a eluting solvent system of methanol/ethyl acetate (10/90 v/v) to give 7α-acetyl-3-benzyl-17-cyclopropylmethyl-6,7,8,14-tetrahydro-6,14-endo-ethenonororipavine (expected yield: 6.9 g; 92% yield).

Example 12

Preparation of 3-benzyl-17-cyclopropylmethyl-6,14-endo-etheno-7α-(2-hydroxy-3,3-dimethyl-2-butyl)-6,7,8,14-tetrahydronororipavine (2-5) from 7α-acetyl-3-benzyl-17-cyclopropylmethyl-6,7,8,14-tetrahydro-6,14-endo-ethenonororipavine (2-4)

To 7α-acetyl-3-benzyl-17-cyclopropylmethyl-6,7,8,14-tetrahydro-6,14-endo-ethenonororipavine (6.6 g, 13 mmol) in dry THF (100 ml) is added tert-butyl magnesium chloride (2.0 M in THF, 8 ml, 16 mmol). The mixture was heated to reflux for 18 hours, cooled, THF (100 ml) is added and mixture is quenched with saturated magnesium sulfate solution. The solution is separated from the semisolids and evaporated in vacuo to dryness to give 3-benzyl-17-cyclopropylmethyl-6,14-endo-etheno-7α-(2-hydroxy-3,3-dimethyl-2-butyl)-6,7,8,14-tetrahydronororipavine (expected yield: 7.5 g; 90% yield).

Example 13

Preparation of buprenorphine from 3-benzyl-17-cyclopropylmethyl-6,14-endo-etheno-7α-(2-hydroxy-3,3-dimethyl-2-butyl)-6,7,8,14-tetrahydronororipavine (2-5)

A mixture of 3-benzyl-17-cyclopropylmethyl-6,14-endo-etheno-7α-(2-hydroxy-3,3-dimethyl-2-butyl)-6,7,8,14-tetrahydronororipavine (7.2 g, 13 m mol), glacial acetic acid (42 ml), and 5% Pd/C (0.36 g) is hydrogenated at 25 psig hydrogen pressure at 40° C. for 16 hours. The catalyst is filtered off and the filtrate evaporated in vacuo to dryness. The residue is re-crystallized from ethanol to give buprenorphine (expected yield: 5.2 g; 86% yield).

Example 14

Preparation of Buprenorphine Hydrochloride

To a solution of buprenorphine (5.1 g, 11 m mol) in ethanol (60 ml) at 50-60° C. is added concentrated hydrochloric acid to pH 2.5, the heating is maintained at 50-60° C. for 2 hours, and cooled to 10-15° C. The mixture is filtered to collect the solid. The solid is washed with cold ethanol and dried at 80° C. under 25 inch Hg of vacuum for 4 hours to give the final product (expected yield: 5.3 g; 96% Yield). This product is identical to a USP standard of Buprenorphine Hydrochloride.

Although the present invention has been described in considerable detail with regard to certain versions thereof, other versions are possible, and alterations, permutations, and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

What is claimed is:

1. A method of preparing buprenorphine or a salt thereof from oripavine comprising:
   reacting the oripavine with methyl vinyl ketone to produce 7α-acetyl-6,7,8,14-tetrahydro-6,14-endoethenooripavine;
   protecting a hydroxyl group of 7α-acetyl-6,7,8,14-tetrahydro-6,14-endoethenooripavine with a benzyl group to 7α-acetyl-3-benzyl-6,7,8,14-tetrahydro-6,14-endoethenooripavine;
   de-methylating the 7α-acetyl-3-benzyl-6,7,8,14-tetrahydro-6,14-endoethenooripavine with ACE-Cl to 7α-acetyl-3-benzyl-6,7,8,14-tetrahydro-6,14-endoethenonororipavine;

alkylating the 7α-acetyl-3-benzyl-6,7,8,14-tetrahydro-6,14-endoethenonororipavine with (chloromethyl)cyclopropane to obtain 7α-acetyl-3-benzyl-17-cyclopropylmethyl-6,7,8,14-tetrahydro-6,14-endoethenonororipavine;

reacting the 7α-acetyl-3-benzyl-17-cyclopropylmethyl-6,7,8,14-tetrahydro-6,14-endoethenonororipavine with tert-butyl magnesium chloride or tert-butyl lithium to produce 3-benzyl-17-cyclopropylmethyl-6,14-endo-etheno-7α-(2-hydroxy-3,3-dimethyl-2-butyl)-6,7,8,14-tetrahydronororipavine; and reducing the 3-benzyl-17-cyclopropylmethyl-6,14-endo-etheno-7α-(2-hydroxy-3,3-dimethyl-2-butyl)-6,7,8,14-tetrahydronororipavine by catalytic hydrogenation to produce buprenorphine.

2. A method of preparing buprenorphine or a salt thereof from oripavine comprising:

protecting a hydroxyl group of oripavine with a benzyl group to 3-benzyloripavine;

reacting the 3-benzyloripavine with methyl vinyl ketone to produce 7α-acetyl-3-benzyl-6,7,8,14-tetrahydro-6,14-endoethenooripavine;

de-methylating the 7α-acetyl-3-benzyl-6,7,8,14-tetrahydro-6,14-endoethenooripavine with ACE-Cl to 7α-acetyl-3-benzyl-6,7,8,14-tetrahydro-6,14-endoethenonororipavine;

alkylating the 7α-acetyl-3-benzyl-6,7,8,14-tetrahydro-6,14-endoethenonororipavine with (chloromethyl)cyclopropane to obtain 7α-acetyl-3-benzyl-17-cyclopropylmethyl-6,7,8,14-tetrahydro-6,14-endoethenonororipavine;

reacting the 7α-acetyl-3-benzyl-17-cyclopropylmethyl-6,7,8,14-tetrahydro-6,14-endoethenonororipavine with tert-butyl magnesium chloride or tert-butyl lithium to produce 3-benzyl-17-cyclopropylmethyl-6,14-endo-etheno-7α-(2-hydroxy-3,3-dimethyl-2-butyl)-6,7,8,14-tetrahydronororipavine; and reducing the 3-benzyl-17-cyclopropylmethyl-6,14-endo-etheno-7α-(2-hydroxy-3,3-dimethyl-2-butyl)-6,7,8,14-tetrahydronororipavine with catalytic hydrogenation to produce buprenorphine.

3. A method of preparing buprenorphine or a salt thereof from oripavine comprising producing 7α-acetyl-6,7,8,14-tetrahydro-6,14-endoethenooripavine.

4. The method of preparing buprenorphine according to claim 3, further comprising obtaining 7α-acetyl-3-benzyl-6,7,8,14-tetrahydro-6,14-endoethenooripavine.

5. The method of preparing buprenorphine according to claim 3, further comprising producing 7α-acetyl-3-benzyl-6,7,8,14-tetrahydro-6,14-endoethenonororipavine.

6. The method of preparing buprenorphine according to claim 3, further comprising converting 7α-acetyl-3-benzyl-17-cyclopropylmethyl-6,7,8,14-tetrahydro-6,14-endoethenonororipavine to produce 3-benzyl-17-cyclopropylmethyl-6,14-endo-etheno-7α-(2-hydroxy-3,3-dimethyl-2-butyl)-6,7,8,14-tetrahydronororipavine.

* * * * *